United States Patent
Lane et al.

(10) Patent No.: US 9,204,822 B2
(45) Date of Patent: Dec. 8, 2015

(54) APPARATUS FOR FUNCTIONAL ELECTRICAL STIMULATION OF THE BODY

(75) Inventors: Rodney Paul Lane, Salisbury (GB);
Darren John Hart, Salisbury (GB);
Stacey Michael Finn, Salisbury (GB);
Paul Nicholas Taylor, Salisbury (GB);
Steven Eric Crook, Fordingbridge (GB);
Ian Douglas Swain, Salisbury (GB)

(73) Assignee: Salisbury NHS Foundation Trust (GB)

( * ) Notice: Subject to any disclaimer, the term of this patent is extended or adjusted under 35 U.S.C. 154(b) by 917 days.

(21) Appl. No.: 13/500,433

(22) PCT Filed: Oct. 6, 2010

(86) PCT No.: PCT/GB2010/051669
§ 371 (c)(1),
(2), (4) Date: Apr. 5, 2012

(87) PCT Pub. No.: WO2011/042736
PCT Pub. Date: Apr. 14, 2011

(65) Prior Publication Data
US 2012/0197343 A1 Aug. 2, 2012

(30) Foreign Application Priority Data
Oct. 6, 2009 (GB) .................................. 0917455.8

(51) Int. Cl.
*A61N 1/00* (2006.01)
*A61B 5/103* (2006.01)
(Continued)

(52) U.S. Cl.
CPC ............. *A61B 5/1036* (2013.01); *A61B 5/6829* (2013.01); *A61N 1/36003* (2013.01); *A61B 5/4519* (2013.01)

(58) Field of Classification Search
CPC ...... A61N 1/36003; A61N 1/36; A61N 3/008
USPC ..................................... 607/48–49
See application file for complete search history.

(56) References Cited

U.S. PATENT DOCUMENTS

| 4,586,510 A | 5/1986 | Glaser |
| 5,350,414 A * | 9/1994 | Kolen .............................. 607/62 |

(Continued)

FOREIGN PATENT DOCUMENTS

| GB | 2368018 A | 4/2002 |
| GB | 2368019 A | 4/2002 |

(Continued)

OTHER PUBLICATIONS

"Great Britain Application Serial No. GB0917455.8, Search Report mailed Apr. 1, 2010", 5 pgs.

(Continued)

*Primary Examiner* — Catherine Voorhees
*Assistant Examiner* — Roland Dinga
(74) *Attorney, Agent, or Firm* — Schwegman Lundberg & Woessner, P.A.

(57) ABSTRACT

A controller is provided for a functional electrical stimulator for attachment to a leg comprising, a connector for a foot switch for sensing foot rise or foot strike, a circuit for responding to said foot switch for generating stimulation pulses and a connector for first and second electrodes for attachment to the leg for supplying stimulation pulses from said circuit The circuit includes a voltage divider of which the foot switch when connected comprises one element, a second element being provided by a digital potentiometer forming part of the controller. A micro controller is configured to make adaptive adjustment of the resistance of said digital potentiometer to take account of the resistance characteristics of the foot switch to provide an output or reference voltage permitting an open/closed state of the switch to be monitored. In an embodiment, manually operable external control devices form part of said controller and the micro controller is configured on operation of said external control devices to change between a working state in which stimulation pulses are provided depending on the state of the foot switch and a setup state for entry using the external control devices of parameters defining characteristics of the stimulation pulses.

16 Claims, 5 Drawing Sheets

(51) Int. Cl.
*A61N 1/36* (2006.01)
*A61B 5/00* (2006.01)

(56) References Cited

U.S. PATENT DOCUMENTS

| | | | |
|---|---|---|---|
| 5,358,513 | A | 10/1994 | Powell, III |
| 5,408,873 | A | 4/1995 | Schmidt et al. |
| 5,546,681 | A | 8/1996 | Goldston et al. |
| 5,643,332 | A | 7/1997 | Stein |
| 5,746,499 | A | 5/1998 | Ratcliffe et al. |
| 5,903,103 | A | 5/1999 | Garner |
| 6,017,128 | A | 1/2000 | Goldston et al. |
| 6,104,140 | A | 8/2000 | Wut |
| 6,507,757 | B1 * | 1/2003 | Swain et al. ............. 607/49 |
| 2003/0060740 | A1 | 3/2003 | Faghri |
| 2006/0282018 | A1 | 12/2006 | Balzano |
| 2007/0112285 | A1 | 5/2007 | Dar |
| 2008/0215114 | A1 | 9/2008 | Stuerzinger |
| 2009/0069865 | A1 * | 3/2009 | Lasko et al. ............. 607/49 |

FOREIGN PATENT DOCUMENTS

| | | |
|---|---|---|
| WO | WO-01/60445 A2 | 8/2001 |
| WO | WO-03/061761 A1 | 7/2003 |
| WO | WO-2007/057899 A2 | 5/2007 |
| WO | WO-2007/125534 A2 | 11/2007 |
| WO | WO-2008/004204 A1 | 1/2008 |
| WO | WO-2008/005865 A1 | 1/2008 |
| WO | WO-2009/018775 A1 | 2/2009 |

OTHER PUBLICATIONS

"International Application Serial No. PCT/GB2010/051669, International Search Report mailed Mar. 23, 2011", 6 pgs.

Burridge, J. H, et al., "Functional electrical stimulation: a review of the literature published on common peroneal nerve stimulation for the correction of dropped foot", *Reviews in Clinical Gerontology*, 8, (1998), 155-161.

Liberson, et al., "Functional electrotherapy in stimulation of the peroneal nerve synchronized with the swing phase of gait of hemiplegic patients", *Arch. Phys. Med. Rehabil.*, 42, (1961), 101-105.

"International Application Serial No. PCT/GB2010/051669, International Preliminary Report on Patentability mailed Apr. 19, 2012", 12 pgs.

"International Application Serial No. PCT/GB2010/051669, Written Opinion mailed Mar. 23, 2011", 10 pgs.

* cited by examiner

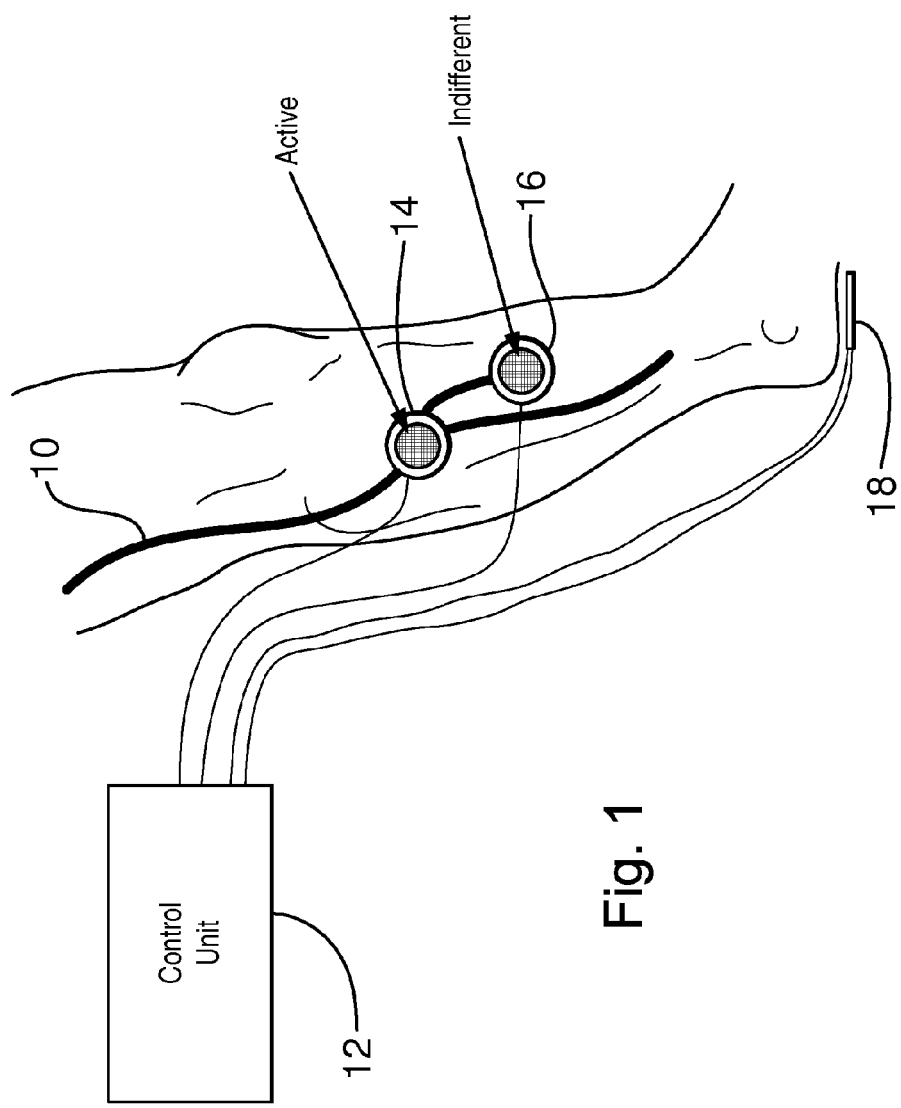

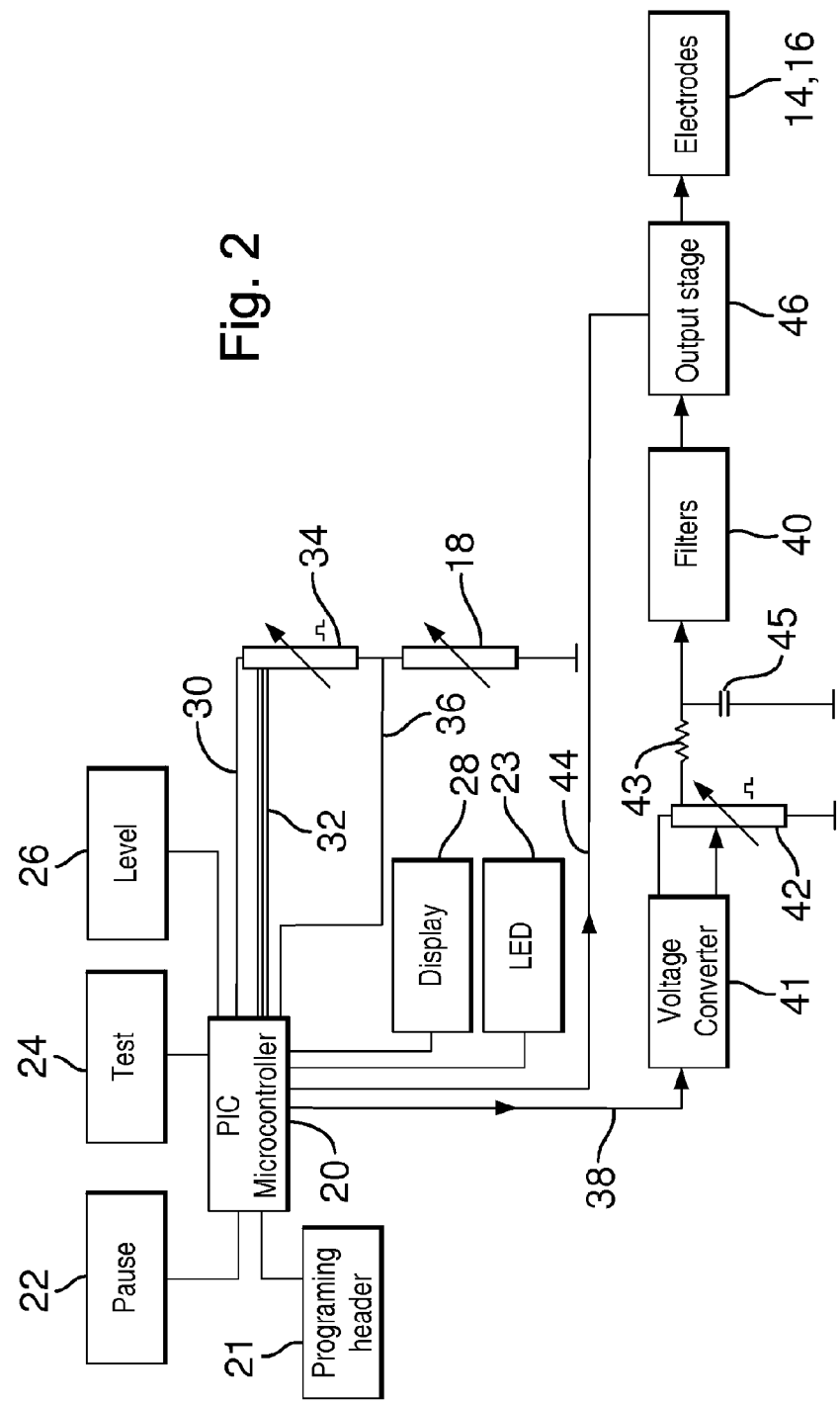

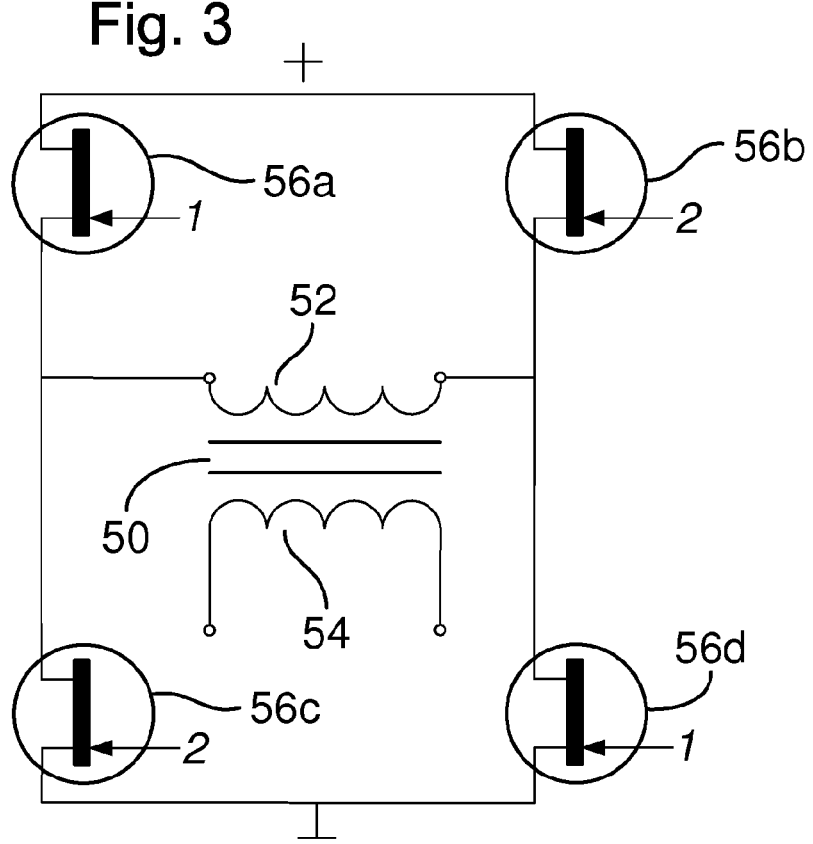
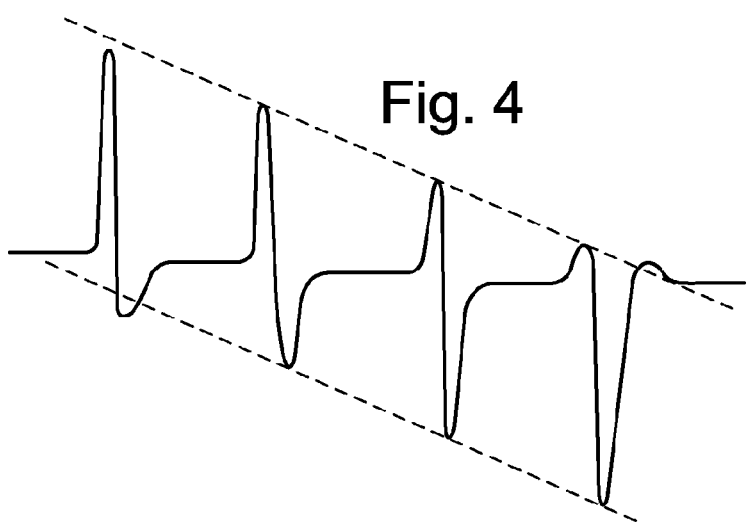

APPARATUS FOR FUNCTIONAL ELECTRICAL STIMULATION OF THE BODY

RELATED APPLICATIONS

This application is a nationalization under 35 U.S.C. 371 of PCT/GB2010/051669, filed Oct. 6, 2010 and published as WO 2011/042736 A1 on Apr. 14, 2011, which claimed priority under 35 U.S.C. 119 to United Kingdom Patent Application Serial No. 0917455.8, filed Oct. 6, 2009; which applications and publication are incorporated herein by reference in their entirety.

FIELD OF THE INVENTION

The present invention relates to a functional electrical stimulator for attachment to the human body for stimulation of one or more muscle groups. It also relates to the use of the stimulator for treating a variety of conditions, in embodiments for treating dropped foot.

BACKGROUND TO THE INVENTION

In embodiments, the invention provides apparatus for applying an electrical stimulus to a person's leg in timed relationship to leg movement during walking in order to achieve a benefit.

For example, a person who has a dropped foot is unable to lift his or her toes clear of the ground during the swing phase of walking. Such a problem is seen in people who have either a peripheral nerve lesion, as a result of trauma or disease, or an upper motor neuron lesion. It is the latter that responds to neuromuscular stimulation. Lesions of the lower motor neurons result in destruction of the neural pathway so that muscle contraction can be achieved only through direct stimulation of the muscle fibers. Functional electrical stimulation may therefore be suitable for the treatment of patients following stroke, multiple sclerosis, spinal cord injury T-12 and above, Parkinson's disease, cerebral palsy, head injury and familial or hereditary spastic paraparesis.

The first reference to functional electrical stimulation (FES) is the work by Liberson et al, "Functional electrotherapy in stimulation of the peroneal nerve synchronized with the swing phase of gait of hemiplegic patients", *Arch. Phys. Med. Rehabil.* 42, 202-205 (1961). At this time electrotherapy was commonplace, but functional electrotherapy was a new concept. Liberson defined it as follows: ' . . . to provide the muscles with electrical stimulation so that at the very time of the stimulation the muscle contraction has a functional purpose, either in locomotion or in prehension or in other muscle activity. In other words, functional electrotherapy is a form of replacement therapy in cases where impulses coming from the central nervous system are lacking.'

Liberson used a portable stimulator to correct drop foot during walking. A train of pulses of 20-250 µsec duration, frequency 30-100 Hz and maximum peak current 90 mA was applied through conductive rubber electrodes. The negative (active) electrode was placed over the common peroneal nerve below the knee and the large indifferent electrode either on the thigh or on the lower leg. The stimulator was worn in the pocket and a heel switch was used to trigger the stimulus during the swing phase of the gait cycle. The switch was worn within the shoe or on the foot on the affected side so that the electrical circuit was interrupted during the stance phase, when the weight was on the heel, and allowed to flow when the heel was lifted during the swing phase. Liberson was enthusiastic about the results, reporting that all the subjects experienced considerable improvement in gait. Despite improvements in the apparatus used, the basic idea of FES has remained unchanged. Sixteen papers on the topic published in the period 1960-1977 have been reviewed by J. H. Burridge et al, *Reviews in Clinical Gerontology*, 8, 155-161 (1998).

U.S. Pat. No. 5,643,332 (Stein) is also concerned with FES and explains that although variants of the technique have been tried and some success has been obtained, the most common appliance fitted to people with foot drop is an ankle-foot orthosis (AFO) which is a plastics brace that fits around the lower leg and holds the foot at close to a 90° angle with respect to the long axis of the leg, and which does not employ electrical stimulation. Stein gives a number of reasons why FES had not replaced the AFO, amongst which is unreliability of the foot switch. In order to overcome this problem, Stein proposes a tilt sensor for measuring the angular position of the lower leg, although he also provides a socket for a hand or foot switch for those patients who cannot use a tilt sensor as there is insufficient tilt of the lower leg. A muscle stimulator for knee stabilization, also based on a tilt switch, is disclosed in U.S. Pat. No. 4,796,631 (Grigoryev). Muscle stimulation for the treatment and prevention of venous thrombosis and pulmonary embolism is disclosed in U.S. Pat. No. 5,358,513 (Powell III).

U.S. Pat. No. 6,507,757 (Swain, the contents of which are incorporated herein by reference) is concerned with improving the reliability of the foot switch. In one aspect it discloses a functional electrical stimulator for attachment to a leg comprising:

first and second electrodes for attachment to the leg to apply an electrical stimulus;

a foot switch for sensing foot rise or foot strike, said foot switch comprising a force-sensitive resistor;

a circuit responsive to said foot switch for generating stimulation pulses; and means forming part of said circuit for responding to changes in the resistance characteristics of said foot switch by adjusting a corresponding response threshold of said circuit.

In an embodiment the value of said force-sensitive resistor reduces from a maximum of about 20 MΩ to a minimum of about 2 kΩ when force is applied to it. The force-sensitive resistor in an embodiment has an active portion comprising an array of fingers in contact with a conductive pad so that mechanical pressure urging the pad towards the fingers reduces the resistance of the switch, the fingers being of a first conductive material e.g. a silver based material and having leads also of said first conductive material, said leads being covered by a second conductive material e.g. a carbon-based material. In an embodiment the circuit comprises potentiometer and a footswitch of variable impedance relative to loading, arranged to form a potential divider. The voltage produced at the point between the two components is measured and tracked when the circuit has been energized. A tracking algorithm is used to determine when the footswitch has been unloaded as the foot is raised from the ground and reloaded when the foot is planted back down. Provision has been made to enable this circuit to be de-energized when the stimulator is placed into sleep mode. Two-channel electrical stimulation is described in GB-A-2368018 (Swain) e.g. for the treatment of bilateral dropped foot.

Footwear with flashing lights controlled by pressure switches is known, see U.S. Pat. Nos. 5,546,681, 5,746,499 and 6,017,128 (L.A. Gear, Inc.), U.S. Pat. No. 5,903,103 (Garner) and U.S. Pat. No. 6,104,140 (Wut).

SUMMARY OF THE INVENTION

In one aspect the invention provides a controller for a functional electrical stimulator for attachment to a leg comprising a connector for a foot switch for sensing foot rise or foot strike, and a circuit for responding to said foot switch for generating stimulation pulses, a connector for first and second electrodes for attachment to the leg for supplying stimulation pulses from said circuit, said circuit including a voltage divider of which the foot switch when connected comprises one element, a second element being provided by a digital potentiometer forming part of the controller; and a microcontroller configured to make adaptive adjustment of the resistance of said digital potentiometer to take account of the resistance characteristics of the foot switch to provide an output or reference voltage permitting an open/closed state of the switch to be monitored.

Embodiments of the above controller have a tracking comparator configured to establish an ambient or threshold level more rapidly than devices made in accordance with U.S. Pat. No. 6,507,757 e.g. within about 3 seconds and thereby providing the possibility of response when the user takes his or her first step.

Embodiments of the above controller are for use with active and indifferent electrodes, in which case the output circuit may include an H-bridge switchable to reverse the active and indifferent electrodes by reversing the polarity of the pulses, in embodiments progressively in a multiplicity of steps e.g. 4, 8, 16 or more steps. The controller may include a microcontroller is configured to apply control pulses to the H-bridge at a frequency in the kHz or MHz range e.g. 200 kHz-10 MHz. The envelope shape of the pulses may conveniently be controlled by pulse width modulation.

In further embodiments the microcontroller may be configured to generate pulses for delivery in at least first and second channels and to supply the pulses through the first and second channels by optically switching a relay having first and second outputs through which electrodes of the first and second channels are connected. It may be configured to generate pulses for delivery in first to fourth channels and to supply pulses to a first optically switched relay having first and second outputs and to second and third optically switched relays connected respectively to the first and second outputs of the first relay and providing outputs for the first to fourth channels. The relay or relays may be controlled by pulses in the kHz or MHz range e.g. at 200 kHz-10 MHz.

In another aspect the invention provides a controller for a functional electrical stimulator for attachment to a leg comprising:

a connector for a foot switch for sensing foot rise or foot strike;

a circuit for responding to said foot switch for generating stimulation pulses;

a connector for first and second electrodes for attachment to the leg for supplying stimulation pulses from said circuit;

manually operable external control devices forming part of said controller; and a microcontroller forming part of said controller and configured on operation of said external control devices to change between a working state in which stimulation pulses are provided depending on the state of the foot switch and a setup state for entry using the external control devices of parameters defining characteristics of the stimulation pulses.

Instructions stored in the microcontroller are configured in the setup state to cause a therapist to input patient-specific parameters for the device in an appropriate pre-determined sequence as indicated below, these instructions being input by the set of manually operable controls forming part of the controller itself. The therapist therefore does not need access to any external device in order to configure the controller for the requirements of an individual patient. In an embodiment those instructions include at least output current, rising ramp time, falling ramp time, output frequency and where more than one footswitch mode is supported the selected mode.

In a further aspect the invention provides a controller for a functional electrical stimulator for generating stimulation pulses for muscles of the human body via active and indifferent electrodes, said having an output including an H-bridge switchable to reverse the active and indifferent electrodes by reversing the polarity of the pulses.

In a yet further aspect the invention provides a controller for a functional electrical stimulator for applying stimulation to muscles of the human body, said controller being configured to generate pulses for delivery in at least first and second channel by optically switching a relay having first and second outputs through which electrodes of the first and second channels are connected. The first channel may be used for control of dropped foot as before, and the second channel may be used, for example, for quadriceps stimulation, to stimulate the gluteus maximus, or to stimulate the triceps and posterior deltoid muscles and improve arm swing. Optical switching has the advantage that each channel is isolated and that there is no cross-talk between channels. The electrodes for the two channels may be connected to the unit via a single stereo-type socket or the like. Three or four channels may be achieved by providing a first switching relay and second and optionally third relays connected to the outputs of the first relay, a second socket being provided for the additional channels.

BRIEF DESCRIPTION OF THE DRAWINGS

How the invention may be put into effect will now be described, by way of example only, with reference to the accompanying drawings, in which:

FIG. 1 shows diagrammatically a functional electrical stimulator according to the invention with electrodes applied to the leg and a foot switch under the user's heel;

FIG. 2 is a simplified block diagram of a first embodiment of a control circuit for the stimulator;

FIG. 3 is a circuit diagram of an output stage of a stimulator according to an embodiment of the invention configured for reversal of active and neutral electrodes connected to the stimulator;

FIG. 4 shows output waveforms from the output stage of FIG. 3 on reversal of the active and neutral electrodes;

DETAILED DESCRIPTION OF PREFERRED EMBODIMENT

Figure 5:
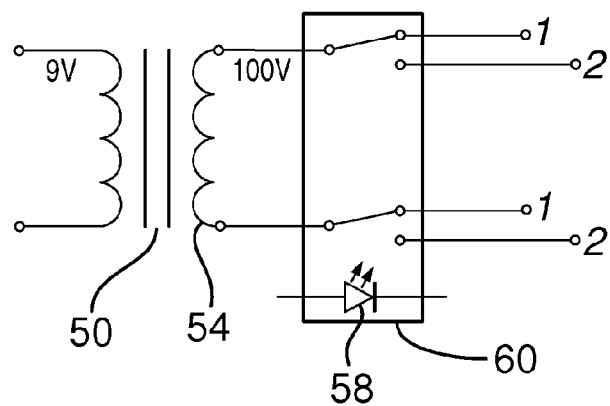
FIG. 5 shows a device for fitting to an output of a stimulator to enable a single stimulator to operate in two channels.

The apparatus disclosed in FIGS. 1 and 2 is an electronic device designed to assist people who have a dropped foot due to neurological damage that inhibits walking. As previously explained, a dropped foot, the inability to lift a foot whilst walking, resulting in the foot being dragged forward or swung out to the side, is a common disability following neurological injury. By stimulating the common peroneal nerve at its most superficial point, passing over the head of the fibula bone, it is possible through excitation of the withdrawal reflex to cause dorsiflexion with degrees of hip and knee flexion. If this is timed with walking using a foot switch worn in the shoe, walking can be significantly improved. The stimulus gives rise to a sensation like "pins and needles" and the patient soon becomes used to it. The apparatus can be made of size e.g. 72×62×26 mm and of weight 112 g including e.g. a PP3 internal battery. It can therefore be small and light enough to be worn in the pocket or on a belt clip. Wires worn under the clothing carry the electrical stimulus to self-adhesive skin surface electrodes on the side of the leg. A small foot switch is placed in the shoe under the heel. The apparatus can be used as an assistive aid or as a training device to strengthen the muscles and achieve voluntary control. Additionally the device has a role in physiotherapy gait re-education, allowing isolated components of the gait cycle to be practiced under the supervision of a therapist. Dorsiflexion and eversion in the swing phase of walking produces reduced tripping and falls, reduced compensatory activity, reduced effort of walking and improved walking speed and a reduction in patient anxiety and depression. The unit is not restricted to the treatment of dropped foot, however, and it may be useful in the treatment of

- gluteal or quadriceps muscles in walking
- gluteal or quadriceps muscles for training weight transfer or sit-to-stand
- hamstrings for increased knee flexion or reduced knee hyperextension
- calf muscles for push-off at terminal stance
- triceps and posterior deltoid for improved arm swing/reduced associated reaction in gait.

One way in which the apparatus can be applied to the user's leg is shown diagrammatically in FIG. 1. The peroneal nerve 10 passes just under the head of the fibula and bifurcates to form deep and superficial branches. An active electrode 14 may be placed over the common peroneal nerve just below the head of the fibula, and an indifferent electrode 16 is located about 5 cm below and slightly medially of the active electrode over the motor point of the anterior tibialis. This is a standard position to produce a flexion withdrawal response.

The positions of the active and indifferent electrodes 14, 16 may be reversed to change the polarity of the stimulation, and in this arrangement in some cases eversion can be decreased while still producing dorsiflexion. The more negative electrode is more effective in producing stimulation than the more positive electrode so that changing electrode polarity controls the site of stimulation. Provision may be made to dynamically vary the polarity across a stream of stimulation pulses such that dorsiflexion and foot inversion/eversion can be controlled during each part of the gait cycle. Such reversal of polarity can permit muscle pairs to be controlled using a single pair of electrodes e.g. to stimulate the deep and superficial branches of the peroneal nerve. The deep branch of the peroneal nerve stimulates a group of muscles including the anterior tibialis which can produce dorsiflexion of the ankle. The superficial branch of the peroneal nerve controls the fibularis longus muscle (also known as peroneus longus) which when injured gives rise to inability to evert the foot and the fibularis brevis (peroneus brevis) muscles and thereby control foot inversion/eversion. The ability to control two groups of muscles by a single pair of electrodes is advantageous from the standpoint of patient compliance because patients find multiple electrodes in the same region of the body tedious to apply. Up to now it has been usual when it is desired to control an additional muscle or group of muscles to add an additional pair of electrodes, which not only increases the amount of equipment that the patient has to wear but also increases the time spent by the patient in fitting and positioning the electrodes each morning.

Foot switch 18 and the electrodes 14, 16 are connected to a control unit 10 that includes controls and circuitry described below.

The foot switch 18 may be as described in U.S. Pat. No. 6,507,757 and in an embodiment comprises a force-sensitive resistor whose resistance reduces from a maximum of about 20 MΩ to a minimum of about 2 kΩ when force is applied to it. The parameters of the foot switch change with time, especially in the harsh environment within a shoe where they are exposed to warmth and moisture and are subject to loads of about 100 Kg that in use are applied and removed typically over $10^4$-$10^6$ cycles. An ordinary potential divider when used to determine the state of the switch gives unreliable results, and it is necessary to adjust the state of the potential divider to take account of these changing parameters as described below. In embodiments, reliable switching may be obtained over a large range of resistance changes in the force sensitive resistor. The voltage divider can be rapidly set when the apparatus is switched on or taken out of sleep mode.

A control circuit for the unit 12 is shown in FIG. 2. The unit is managed by a PIC microcontroller 20 which has a stored program input by a programming header 21 and aspects of which can be adjusted by a therapist for an individual patient. An 8-bit microcontroller suffices and may in an embodiment be a microcontroller of the PIC18F4685 family available from Microchip Technology Inc which have 96 KB of readable, writeable and erasable flash program memory, a 10-bit A/D converter, and features that reduce power consumption and extend battery life. These include a sleep mode and alternate run modes that permit power consumption during code execution to be reduced by up to 90%, multiple idle modes including modes where the CPU runs with its core disabled but peripherals still active allowing power consumption to be reduced to as low as 4% of normal requirements. One such mode is for timing sensitive applications, and allows for fast resumption of device operation with its more accurate primary clock source, since the clock source does not have to "warm up" or transition from another oscillator. In a SEC_IDLE mode the CPU is disabled but the peripherals continue to be clocked from the Timer1 oscillator. In RC_IDLE mode, the CPU is disabled but the peripherals continue to be clocked from the internal oscillator block using the INTOSC multiplexer. This mode allows for controllable power conservation during idle periods. The programming header 21 permits in system programming of firmware including, as previously explained, parameters later set by the therapist using the user interface of the device.

The unit 12 has a number of sockets and controls for the user. A jack socket is provided for the foot switch 18. An electrode jack socket of size different from the foot switch socket is provided. A combined stimulation level and on/off switch 26 enables the contraction strength to be controlled by adjusting the stimulation pulse width from 10 to 400 μs. The switch 26 in an embodiment takes the form of a control knob which can be depressed and held down to turn the unit on and can be rotated clockwise or counterclockwise to increase or decrease the output level. An output test button 24 enables electrode positions to be tested by the therapist and by the user and can be used by the therapist when the stimulator is being used during exercising to practice components of gait. An output is given when the button is pressed when the apparatus is being used in heel strike mode or when the button is released if it is being used in heel rise mode. When testing the condition of the footswitch is not monitored and so the loading on the switch has no influence on the test. An output indicator LED 23 flickers when the unit has been triggered. A pause switch 22 is provided that when the unit is in walk or exercise mode may be used to start and stop operation of the unit when pressed puts the apparatus into sleep mode, which will conserve the battery when the user sits down. To return the unit to its active state, the user need only press the pause switch 22 again. A bleep is heard, and then the apparatus again responds to the foot switch. The unit can only be turned off when its output has been paused, otherwise there is a risk of it being turned off accidentally while in use. When the pause button 22 has been depressed to put the unit into pause mode, the switch is rotated to its minimum position and then depressed. An advantage of this feature is that when the unit is turned off, the pulse width setting is reduced e.g. to 1%. The user must reset the level to resume use of the unit. It has been found in practice that users turn the device up through the day as their muscles become tired and having to reset the stimulation level when the device is newly turned on means that they do not receive an unexpectedly high level of stimulation when they turn the device on the next day. The recommendation for patients is that the unit should therefore not be turned off using the control knob through the day but put into sleep mode using the pause switch.

When the unit has been turned on and is paused, a setup routine forming part of the program stored in microcontroller 20 can be accessed. This may be e.g. by depressing and holding down the switch 26 and within a predetermined period operating both the pause switch 22 and the test button 24.

The first time that the set-up mode is entered after turning on the device, a setup menu is presented inviting the clinician to select the condition to be treated e.g. dropped foot or one of the other conditions set out above. When this selection has been made, the setup routine progresses to a fine tuning menu shown on display 28 in which the following parameters are adjusted in the sequence indicated:

Output current (in an embodiment adjustable between 10 and 100 mA, default 10 mA with a pulse width of 50%). The user may increase contraction strength by increasing the pulse width, compensating for day to day variations in muscle fatigue, electrode position and battery condition or changes in muscle tone. In FIG. 2, signals from the microcontroller 20 pass through voltage converter 41, digital potentiometer 42, a network comprising current limiting resistor 42 and capacitor 45, filters 40 and output stage 46 to electrodes 14, 16. The output stage may also be controlled by the microcontroller via lines 44. In one embodiment the output stage comprises a push-pull converter having an output transformer whose primary is controlled by a pair of 2N7002 and IRF7317 FETs and whose secondary is connected across the electrode socket. In another embodiment shown in FIG. 3, output transformer 50 has a primary 52 connected into an H-bridge of four FETs 56a-56d and a secondary 54 for connection to the electrodes. Current may pass through transistors 56a, 56d on supply of signals to gate inputs 1, or may flow through transistors 56b, 56c on application of signals to gate inputs 2. The transistors 56a-56d are pulse width modulated to achieve a desired waveform and are operated in a region where they exhibit analog-type gate voltage-response behavior. Modulating pulses are applied to their gates through lines 44 at frequencies which in some embodiments are in the range 200 KHz-10 MHz e.g. 2 or 8 MHz. At these frequencies the internal capacities of the transistors which are of the order of a few picofarads smooth the output waveform.

As is apparent from FIG. 4 which shows in a simplified diagram output waveforms during a single switching operation, the output waveform is such that the pulses can be switched progressively from energizing one electrode as active electrode to energizing the other electrode as active electrode, the change conveniently being stepwise in 4, 8 or 16 steps, over-rapid switching from one site of stimulation to the other being undesirable from the standpoint of the patient.

Electrical pulses applied to the body via skin surface electrodes cause depolarization of the underlying nerve membrane, which causes the propagation of an impulse along the nerve and contraction of the associated muscle. The response of the nerve depends on the properties of the applied stimulus. If the stimulus is too short, high stimulus amplitude is required to bring about depolarization, and the amplitude of the stimulus required can be reduced by increasing the threshold, but only up to a maximum. The most efficient length of impulse is about 300 μs with little decrease in threshold beyond 1 ms, the required currents being about 15-150 mA. A chain of pulses is required to produce a fused tetanic contraction. As the pulse repetition frequency is increased, the individual contractions of the muscles being stimulated become closer together until at about 10 Hz fused contraction is achieved. However, the user will still be aware of vibration due to the individual pulses. By about 20 Hz vibration is reduced and a frequency of 30-40 Hz avoiding the user becoming aware of individual pulses while not resulting in rapid muscle fatigue. A frequency of 40 Hz is suitable for eliciting reflexors. An appropriate frequency can be selected for individual patients. By slowing the rising and falling edges of the stimulation envelope, the stimulus can be made more comfortable for the patient, a ramp time of 1-2 s being suitable but some users with severe spasticity requiring a ramp time of 6 s or above.

Rising ramp (0-2000 ms, default 200 ms) which allows the clinician to choose how rapidly the stimulation rises to its maximum pulse width once a stimulation output starts. There are three reasons for adjustment of this parameter. In patients with spasticity in their calf muscles, a rapid rise in pulse width may cause a rapid stretch of the calf, which may result in a stretch reflex that opposes dorsiflexion and may appear as a general stiffening of the calf or clonus spasm. A longer ramp helps to prevent this happening. Some patients find a rapid rise of pulse width uncomfortable. A longer ramp may be more acceptable. If dorsiflexion occurs too soon, it is difficult for a patient to use his or her calf muscles to push forward at terminal stance. A longer ramp may allow this to happen. However, in all cases it is important that the stimulation ramps fast enough to cause dorsiflexion when the foot is lifted. For this reason, faster walkers will require shorter ramps.

Extension (0-2000 ms, default 200 ms) which allows a period of stimulation after weight is returned to the heel switch (or taken off it in heel rise mode) to be added. This enables an eccentric contraction in the anterior tibialis, lowering the foot to the ground. If the extension is too short, the ankle may lack control at the weight acceptance phase of walking and audible slap may occur as the foot strikes the ground. Extension can also be used to provide eversion for ankle stability in initial weight bearing when there is excessive inversion.

Falling ramp (0-2000 ms, default 200 ms) is the interval during which the pulse width takes to reach zero after the Extension has ended. It can be used with the extension to control the movement of the foot after heel strike and increase comfort.

Time out period (300-6000 ms) is the maximum time that stimulation can last for from a single footswitch or test switch trigger. It may be set just a little longer than the longest stride time taken by the user and is desirably long enough for activities such as stair climbing but not so long that a user will be subject to prolonged stimulation when weight is taken off the switch on sitting down.

Output waveform may be selected from symmetric and asymmetric. When an asymmetrical biphasic waveform is used, the strongest stimulation effect is under the active electrode. Placing the active electrode over the common peroneal nerve and indifferent over the anterior tibialis generally produces dorsiflexion with eversion. Swapping the electrodes around gives more dorsiflexion and less eversion (see the discussion above). In Symmetrical biphasic, the polarity of every other pulse is reversed so that both electrodes have equal stimulation effect. For some users this may produce a better balance of eversion and inversion. Some people find this waveform more comfortable and/or are less prone to skin reaction. The waveforms in FIG. 4 show pulses with regions of opposite polarity but less than completely symmetrical so that the balancing pulse is less than the main pulse, waveforms of this type being found to be effective and avoiding skin irritation for many users. If the polarity of the electrodes is swapped over diring the dourse of a stream of stimulation pulses the degree of balance between dorsiflexion and eversion can be controlled for each part of the gait cycle. The same method will also work if the stimulator is used for other muscle groups of the body e.g. in upper limb applications where the stimulator may be used with an alternative trigger to the footswitch 18.

Frequency (20-60 Hz, default 40 Hz for dropped foot) may be selected to reduce muscle fatigue and improve response e.g. in MS patients who may benefit from higher or lower frequencies within the above range.

Foot switch operation on heel strike or heel rise. For dropped foot correction, heel rise is more commonly used. The foot switch may be placed under the heel of the affected side. This means all the equipment is on the same side of the body and is considered more convenient by most users. However, if foot contact is unreliable on the affected side, it can be more effective to place the foot switch under the heel on the opposite side which may give a more reliable trigger. In this case stimulation needs to begin when weight is applied to the switch so the heel strike setting is used. Some faster walkers also prefer this mode.

Timing mode. Adaptive Timing is a mode where stimulation is started by a foot switch change (e.g. heel rise or heel strike) and ended by a foot switch change (e.g. heel strike or heel rise). If the second footswitch change does not occur before the set Time Out Period, stimulation will end automatically. This timing mode adapts well to walking speed changes and is used in most default settings including dropped foot. Fixed time mode stimulation starts on a footswitch change (e.g. heel rise or heel strike) but is ended after a fixed time set by a time out period. This mode is used when foot contact is inconsistent and gives unreliable triggering. It can be useful if the user is hesitant in taking steps, taking weight on and off the footswitch as multiple attempts are made. No time out: mode is similar to adaptive timing except there is no maximum time for stimulation output which simply follows the footswitch. An extension may still be added to the end of the stimulation output. This mode is not normally used in dropped foot correction but may be used for stimulating anti gravity muscles such as quadriceps or gluteus maximus.

Figure 7:
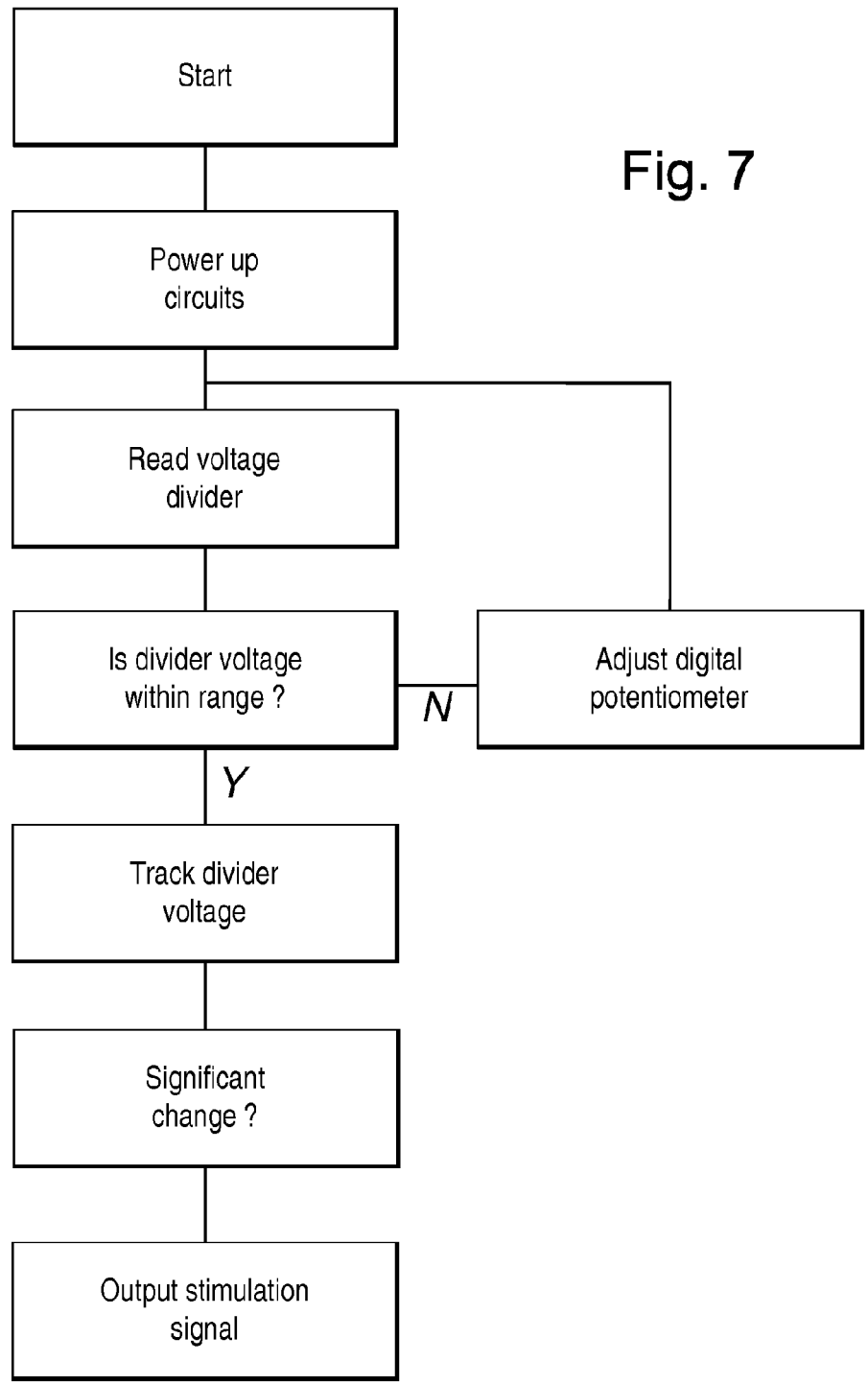
FIG. 7 is a simplified flow chart illustrating how a voltage divider forming part of the control circuit of FIG. 2 is adjusted to maintain the output at a suitable voltage for monitoring the state of the foot switch.

In FIG. 2 a voltage divider formed by foot switch 18 and digital potentiometer 34 controlled by lines 32 from the microcontroller 20 form a voltage divider connected between voltage rail 30 and earth. The output is connected at 36 to an A/D converter input of the microcontroller 20. The value of the potentiometer 34 is set to maintain the voltage at 36 at a level such as to permit reliable detection of the open/closed state of foot switch 18, the necessary value depending on the resistance of the switch 18 which is variable according to the conditions to which the switch is subject. Although the switch 18 is recommended to be fitted to the underside of a cork insole, variability in the conditions to which the switch is subject is unavoidable. The routine executed by the microcontroller as regards the voltage divider is shown in FIG. 7 which is believed to be self-explanatory.

The stimulator may be used for exercise prior to or as well as for functional use. It may be used to treat other muscle groups e.g. those of the upper limb e.g. the deltoid and triceps muscles which can be stimulated using the scheme for switching active electrodes shown in FIGS. 3 and 4. The footswitch trigger may be replaced with other forms of trigger e.g. positional or proximity switches. Multiple stimulators may be linked with wires or wirelessly to treat complex conditions e.g. hemiplegia.

Figure 6:
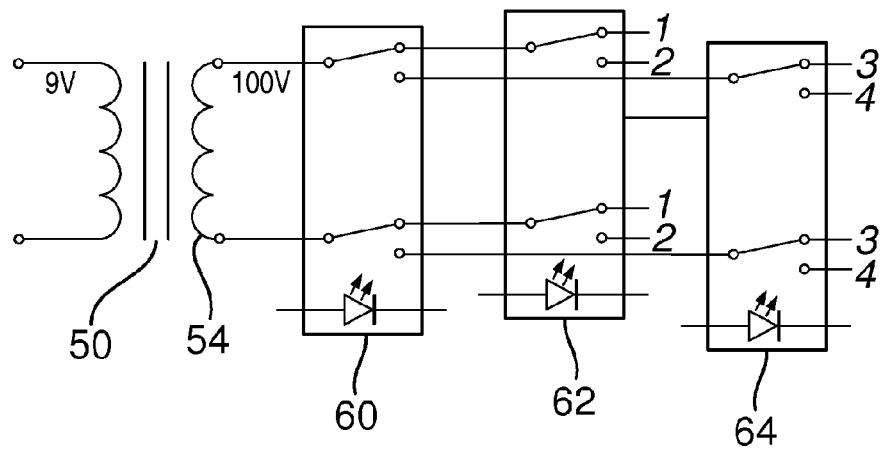
FIG. 6 shows a device for fitting to an output of a stimulator to enable the device to operate in four channels.

FIG. 5 shows an arrangement for two channel stimulation. Output pulses are fed to the primary of output transformer 50 whose secondary 54 is connected to optical relay 60 switchable between first and second output states depending on whether photodiode 58 is energized. In FIG. 6 the outputs of the first optical relay are connected to second and third optical relays 62, 64 to provide outputs for four channels.

It will be appreciated that variations may be made in the embodiments described herein without departing from the invention.

The invention claimed is:

1. A controller for a functional electrical stimulator for attachment to a leg comprising:
    a connector for a foot switch for sensing foot rise or foot strike; and
    a circuit for responding to reduction of resistance of said foot switch when force is applied to the foot switch for generating stimulation pulses;
    a connector for first and second electrodes for attachment to the leg for supplying stimulation pulses from said circuit,
    said circuit including a voltage divider of which the foot switch when connected comprises one element, a second element being provided by a digital potentiometer forming part of the controller; and
    a microcontroller configured to make adaptive adjustment of the resistance of said digital potentiometer to take account of the resistance characteristics of the foot switch to provide an output or reference voltage permitting significant changes in the state of the switch to be monitored, values for parameters of the foot switch varying over time, and a state of the voltage divider being adjustable responsive to variation in values of parameters of the foot switch.

2. The controller of claim 1, wherein the microcontroller has an A/D converter input and the output of the voltage divider is connected to that input.

3. The controller of claim 1, further comprising an output circuit having a second digital potentiometer controlled by the microcontroller for controlling the magnitude of the electrical stimulus applied to the leg.

4. The controller of claim 3, wherein said electrodes are active and indifferent electrodes and the output circuit includes an H-bridge switchable to reverse the active and indifferent electrodes by reversing the polarity of the pulses.

5. The controller of claim 4, configured to reverse the polarity progressively in a multiplicity of steps.

6. The controller of claim 4, wherein the microcontroller is configured to apply control pulses to the H-bridge at a frequency in the kHz or MHz range.

7. The controller of claim 6, wherein the microcontroller is configured to apply control pulses to the H-bridge at a frequency of 200 kHz-10 MHz.

8. The controller of claim 1, wherein the microcontroller is configured to control the envelope shape of the pulses applied to the body using pulse width modulation.

9. The controller claim 1, wherein the microcontroller is configured to generate pulses for delivery in at least first and second channels and to supply the pulses through the first and second channels by optically switching a relay having first and second outputs through which electrodes of the first and second channels are connected.

10. The controller of claim 9, including a microcontroller configured to apply control pulses to the relay at a frequency of 200 kHz-10 MHz.

11. The controller of claim 1, wherein the microcontroller is configured to generate pulses for delivery in first to fourth channels and to supply pulses to a first optically switched relay having first and second outputs and to second and third optically switched relays connected respectively to the first and second outputs of the first relay and providing outputs for the first to fourth channels.

12. The controller of claim 1 having controls operable to cause the microcontroller to change between a working state and a setup state of parameters defining characteristics of the stimulation pulses.

13. The controller of claim 1, further comprising a foot switch.

14. The controller of claim 13, wherein the foot switch is a force-sensitive resistor whose value reduces from a maximum of about 20 MΩ to a minimum of about 2 kΩ when force is applied to it.

15. A controller for a functional electrical stimulator for generating stimulation pulses for muscles of the human body via active and indifferent electrodes, said having an output including an H-bridge switchable to reverse the active and indifferent electrodes by reversing the polarity of the pulses, said controller including
  a foot switch for sensing foot rise or foot strike; and
  a circuit for responding to reduction of resistance of said foot switch, said circuit including a voltage divider including a digital potentiometer; and
  a microcontroller configured to make adaptive adjustment of the resistance of said digital potentiometer to take account of the resistance characteristics of the foot switch to provide an output or reference voltage permitting significant changes in the state of the switch to be monitored, values for parameters of the foot switch varying over time, and a state of the voltage divider being adjustable responsive to variation in values of parameters of the foot switch.

16. The controller of claim 15, comprising FETs configured with an output transformer as the H-bridge, the FET's being biased so as to provide an output proportional to the signal applied to their gates.

* * * * *